US008007900B2

(12) United States Patent
Hoekstra et al.

(10) Patent No.: US 8,007,900 B2
(45) Date of Patent: Aug. 30, 2011

(54) LIGHT ABSORBING LAYER FOR PHOTO-CHROMIC SYSTEMS

(75) Inventors: Kathleen Hoekstra, Newark, DE (US); David Nichols, Wilmington, DE (US); Ross Birney, Paisley (GB)

(73) Assignee: BASF SE, Ludwigshafen (DE)

( * ) Notice: Subject to any disclaimer, the term of this patent is extended or adjusted under 35 U.S.C. 154(b) by 913 days.

(21) Appl. No.: 11/977,197

(22) Filed: Oct. 24, 2007

(65) Prior Publication Data

US 2008/0167183 A1  Jul. 10, 2008

Related U.S. Application Data

(60) Provisional application No. 60/854,931, filed on Oct. 26, 2006.

(51) Int. Cl.
*B32B 3/00* (2006.01)
*B32B 5/16* (2006.01)
*B32B 7/00* (2006.01)

(52) U.S. Cl. ...... 428/207; 428/213; 428/412; 428/423.1; 428/446; 428/473.5; 428/474.4; 428/480; 428/484.1; 428/500; 428/913

(58) Field of Classification Search .......... 428/207, 428/213, 412, 423.1, 446, 473.5, 474.4, 480, 428/484.1, 500, 913
See application file for complete search history.

(56) References Cited

U.S. PATENT DOCUMENTS

| 4,522,881 A | 6/1985 | Kobayashi et al. ........... 428/336 |
| 5,756,356 A | 5/1998 | Yanagi et al. .................... 436/7 |
| 6,184,375 B1 | 2/2001 | Hüglin et al. ................. 544/116 |
| 6,524,000 B1 | 2/2003 | Roth ............................. 374/102 |
| 6,544,925 B1 | 4/2003 | Prusik et al. .................. 503/201 |
| 6,547,390 B1 | 4/2003 | Bernheim et al. ............ 351/163 |
| 6,746,666 B1 | 6/2004 | Luther ............................ 424/59 |
| 6,855,666 B2 | 2/2005 | Simpson et al. .............. 503/227 |
| 7,081,364 B1 | 7/2006 | Haarer et al. ................. 436/164 |
| 2002/0072472 A1 | 6/2002 | Furuya et al. ................. 503/201 |
| 2006/0130734 A1 | 6/2006 | Koivukunnas et al. ....... 116/216 |
| 2006/0145091 A1* | 7/2006 | Patel ......................... 250/474.1 |

FOREIGN PATENT DOCUMENTS

| EP | 0117390 | 9/1984 |
| WO | 2005/016654 | 2/2005 |
| WO | 2005/075978 | 8/2005 |
| WO | 2006/001801 | 1/2006 |

* cited by examiner

*Primary Examiner* — Betelhem Shewareged
(74) *Attorney, Agent, or Firm* — Qi Zhuo

(57) ABSTRACT

A composition which comprises a light absorbing layer adhered to an underlying layer containing a photo-chromic colorant, which photo-chromic colorant has been activated by exposure to UV light to undergo a reversible color change, and wherein the rate of color reversion is dependent on temperature, is provided. The ultraviolet light and/or visible light absorbing layer may also contain components which reflect rather than absorb light and can be conveniently applied via thermal transfer or ink jet to a substrate comprising the photo-chromic colorant to protect it from unwanted exposure to UV and/or certain wavelengths visible light. The composition is conveniently employed in a temperature time indicator (TTI).

11 Claims, No Drawings

LIGHT ABSORBING LAYER FOR
PHOTO-CHROMIC SYSTEMS

This application claims benefit under 35 USC 119(e) of U.S. provisional application No. U.S. Ser. No. 60/854,931 filed Oct. 26, 2006.

A photo-chromic composition is provided wherein a light absorbing layer is adhered to an underlying substrate or layer containing a photo-chromic colorant, which photo-chromic colorant has been activated by exposure to UV light to undergo a reversible color change, which color reversion occurs at a rate that is dependent on temperature, and wherein the rate of color reversion is dependent on temperature. The light absorbing layer can be conveniently applied via thermal transfer or ink jet to a substrate comprising the photo-chromic colorant to protect it from unwanted exposure to UV and/or certain wavelengths visible light.

Photo-chromic, thermo-chromic and electro-chromic materials are all known and widely used in a variety of commercial applications. These "X-chromic" materials are those which change color, that is, their absorbance and transmission of visible light, when exposed to the particular stimulant. For example, a photo-chromic material changes color when exposed to certain wavelengths of light, for example UV light; a thermo-chromic material changes color when exposed to a certain amount of heat; an electro-chromic material changes color when exposed to certain electrical voltages.

Naturally other changes may occur when these materials are exposed to the particular stimulant, e.g., molecular structure, conductivity, infra red absorption, UV absorption etc., however, it is the observable change in color, and the factors that impact the color changes of photo chromic materials that are of interest in this invention.

Photo-chromic materials, for example photo-chromic dyes and pigments, change color when exposed to specific wavelengths of light, i.e., activating light, and then revert to their original color when no longer exposed to these wavelengths. The color change may be from one color to another, or from a non-colored material to a colored material or vice versa. One example of commercial photo-chromic materials are eye glasses that darken when exposed to the UV component of outdoor sunlight and then revert to a non-colored form when the wearer goes inside where less UV light is present, or when the sun sets and the skies darken.

There is a period of time associated with both the change or formation of color when the photo chromic material is exposed to the activating light, and with the reversion to the original color. Knowledge of how long it takes for color reversion to occur under specific conditions, and an understanding of the factors that influence the rate at which this change occurs, allow one to use the color change process as a measure of time and the cumulative impact of surrounding conditions.

For example, if an article becomes colored when exposed to activating UV light and it is known that it will take a certain period of time at room temperature to revert to a clear state, one can tell whether such a period of time has passed since UV exposure by simply looking at the article. Obviously, if the photo-chromic material is re-exposed to the activating UV light during the period in which reversion takes place, the time period for reversion becomes extended.

Color-changing or color-forming temperature sensitive indicators for monitoring of handling of perishable goods are well known in the art. Such perishable goods are for example foodstuffs, pharmaceuticals, biological materials, chemical substances, coating compositions, adhesives, cosmetics, food additives, photographic supplies and vaccines. Several time-temperature integrating indicator systems and devices have also been proposed. There is a growing interest for indicator systems and devices for monitoring a temperature and a time as an accumulated value of articles, which are stored at a constant temperature for a certain period of time. Particularly such indicator systems are used for signaling when the articles have reached the point of quality loss or unsafe condition due to excessive temperature exposures.

Commercially available are temperature time indicators, also known as TTIs, which employ enzymatic color indicators to show the amount of higher temperature exposure of a stored or shipped temperature-sensitive commodity. The enzyme indicator is activated at the beginning of a monitoring period by applying pressure on a plastic bubble strip thus releasing the enzyme, substrate and indicator to react with each other. Another indicator system based on a polymerization reaction; however this system must be stored frozen prior to usage. Also a product based on a dyed wax that diffuses along a strip of paper is known.

Recently, it has been found that UV activated photo-chromic colorants, such as photo chromic dyes and pigments, can be used in such conceptually simple, and readily processable, timing devices. For example, it is known how much faster the color reversion of certain photo-chromic colorants occurs at higher temperatures and the rate of reversion can be calculated over a varying temperature profile. Thus, a temperature time indicator (TTI) can be prepared based on the cumulative effect of time and temperature on the color change of photo-chromic colorants which occurs after exposure to activating light.

U.S. Pat. No. 7,081,364, incorporated herein in its entirety by reference, discloses such TTIs.

However, after exposure to activating light, i.e., light activation, one must take care to ensure that the activated pigment does not get further exposed to activating light as this will compromise the calculated time period for reversion. The TTIs of U.S. Pat. No. 7,081,364 are protected against additional light exposure by a yellow cellophane film or other yellow polymer applied after initial activating UV radiation. Better solutions to this problem are needed.

This problem is solved by the present invention which provides a light absorbing layer that protects an underlying layer which contains a photo-chromic colorant activated by exposure to UV light. The light absorbing layer is conveniently applied by thermal transfer, hot stamp or ink jet processes, both processes currently common in printing applications. The light absorbing layer therefore protects the color reversion process from being interrupted by additional and unintended exposure to activating light, thus ensuring the accuracy of the calculated temperature dependent rate of color reversion.

U.S. Pat. No. 6,855,666, incorporated herein in its entirety by reference, discloses protecting printed, dye based images from UV induced fade with a heat transferable protective overcoat comprising 2-30% by weight of a hydroxyphenyl triazine UVA in a polymeric binder.

U.S. Pat. No. 4,522,881, incorporated herein in its entirety by reference, discloses a cover film comprising a heat resistant base and a transparent UV shielding layer wherein the UV shielding layer is transferred to a paper by heat.

Both U.S. Pat. Nos. 6,855,666 and 4,522,881 relate to the common practice of protecting dye-based images from photo-fade with an over laminate that absorbs UV light.

US Pub. Pat. Appl. No. 20060130734, incorporated entirely by reference discloses printed time-temperature integrating indicators, also known as TTI indicators, which is printed on substrates, such as packaging materials. The TTI comprises an optional protective layer on the substrate, a diffusion layer, agent A and agent B on the substrate or on the protective layer or on the diffusion layer, an optional outer protective layer, and an optional outer substrate layer. The printed TTI indicator is selectively activated at the time of packaging of a perishable product or alternatively at the time of opening of the package of a perishable product by bring agents A and B into contact with each other.

U.S. Pat. No. 5,756,356, incorporated herein in its entirety by reference, discloses an indicator material and a method of indicating a time or a temperature time accumulated value as a color change which comprises providing an oxidation-polymerizable dyestuff (agent A) and oxidizing agent (agent B) in a non-contact state and the agent A and/or the agent B being held in a carrier which may be a resin or liquid media.

A recording material is provided in EP 1048477, incorporated herein in its entirety by reference, which material is suitable for use in a direct thermal imaging apparatus and which contains at least one indicator compound that is convertible from an inactive state to an active state by the application of heat with a direct thermal imaging apparatus.

WO 01/64430, incorporated herein in its entirety by reference, discloses an indicator system, which is attached to a unit of thermally sensitive perishable product. Said indicator system comprises use of a direct self-adhesive thermal label paper comprising a color-forming high-temperature printing composition, and a second activating element component in the form of a self-adhesive tab or label comprising a substrate, an adhesive composition and an activating component that, when applied to the direct thermal coating, combines with the primary composition to enable its color-forming reaction.

SUMMARY OF THE INVENTION

This invention provides a light absorbing layer which functions as a UV-VIS protective filter to prevent the unintended charging, also referred to herein as activating, of photo-chromic materials. "Charging" or "activating" photochromic materials refers to the reversible color change brought about by the exposure of photochromic colorants to certain wavelengths of UV or visible light.

The light absorbing layer of course does not stop all light but rather it blocks enough of the activating light so that the underlying layer is not re-activated during use. The light absorbing layer also blocks light, for example UV light and certain wavelengths of visible light, in a variety of ways, for example the light may be absorbed or reflected by the components of the "light absorbing" or "light blocking" layer, therefore, either term can be used to designate the light absorbing layer of the invention.

The light absorbing layer can be conveniently printed over the light sensitive material, for example, via digital printing and other printing methods such as thermal transfer, hot stamp, and ink jet printing. A useful feature of the invention is that these methods allow high speed, in-line application of the light absorbing layer over a substrate containing the light sensitive material. In the case of thermal transfer printing or hot stamp, the UV-VIS filter composition is coated onto a carrier ribbon which is then used in thermal transfer printing or hot stamp to deliver the UV-VIS filter composition over the light-sensitive material. In the case of inkjet delivery of the filter, the UV-VIS filter composition is a wet ink delivered by an inkjet print head or spray nozzle.

DETAILED DESCRIPTION OF THE INVENTION

Provided is a composition comprising a light absorbing layer which is adhered to an underlying substrate which underlying substrate comprises a photo-chromic colorant, which photo chromic colorant is activated by exposure to UV light to undergo a reversible color change, which color reversion occurs at a rate that is dependent on temperature, wherein the light absorbing layer comprises a binder, said binder comprising a wax, a natural polymer and/or a synthetic polymer and from about 1 to about 60% by weight, for example greater than 30% by weight, for example about 35-60% by weight, based on the total weight of the layer, of a light absorbing composition which light absorbing composition comprises one or more components selected from the group consisting of hydroxyphenylbenzotriazole, benzophenone, benzoxazone, α-cyanoacrylate, oxanilide, tris-aryl-s-triazine, formamidine, cinnamate, malonate, benzilidene, salicylate and benzoate ultraviolet light absorbers and wherein the light absorbing layer is sufficiently transparent in the visible light region to allow the reversible color change of the photochromic material to be visible.

The light absorbing layer is typically adhered to an underlying substrate containing the photo-chromic colorant wherein the colorant has already been exposed to the activating UV light. Color reversion is the process wherein the photo-chromic colorant reverts to its color of the photo-chromic colorant absent UV light exposure. In such instances it is generally desirable to apply the light absorbing layer as soon as possible after exposure of the photo-chromic colorant to UV light. The amount and wavelengths of the UV light is predetermined and dependent on the photo-chromic colorant present.

The underlying substrate containing the photo-chromic colorant may itself be a layer applied to a substrate.

In one embodiment, the light absorbing layer is applied immediately after UV exposure of the underlying substrate photo-chromic colorant, for example, as part of a single multi-step process which occurs on a single machine or multiple machines which are directly connected to allow for the rapid and continuous execution of the multi-step process comprising UV exposure and application of the light absorbing layer.

If the underlying substrate photo-chromic colorant is charged after the light absorbing layer has been applied, the intensity of the charging light must be high enough to overcome the blocking power of the light absorbing layer.

When referring to the amount of light absorbing composition in the light absorbing layer, the weight percentages given refer to the weight percent based on the light absorbing layer solids. That is, any volatile materials which evaporate upon or after application of the layer, such as solvents that may be used in the preparation of the light absorbing layer, are not part of "the total weight of the layer".

The ultraviolet light absorbers, also referred to as UVAs, are widely known compounds and many are commercially available. The amount of UVA present in the light absorbing layer depends in part on the thickness of the layer. A thin layer will require a higher concentration of UVA to absorb the same amount of UV light as a thick layer. Typically, relatively thin layers will be preferred for economic, storage, packaging and processing reasons and concentrations of UVA of 35%-60% by weight based on the total weight of the layer allow for the layers to be in the form of thin films. For example the layers are from about 0.1 to about 1,000 microns thick, but films between about 1 and 500 microns or between about 2 and about 100 microns or less are desirable. For example, the light absorbing layer is from about 0.1 to about 50 microns thick.

In one embodiment the light absorbing layer is from 2 to 100 microns thick and contains from about 35 to 60% by weight, based on the total weight of the layer, of UVA.

In another embodiment the light absorbing layer is from 0.1 to about 50 microns thick and contains from about 35 to 60% by weight, based on the total weight of the layer, of UVA.

The goal in formulating the light absorbing layer is to obtain adequate coverage of the light absorbing composition over the area that needs protection. A measure of coverage is the weight per unit area of light absorbing composition of the final layer, that is, the light absorbing layer after all processing is complete and volatiles have been removed. For example, a thick layer with a low concentration of light absorbing composition can be comparable in weight per unit area as a thin film with a high concentration. Typically, the weight per unit area of light absorbing composition in the light absorbing layer will be from about 0.7 g/m$^2$ (that is, 0.7 grams per square meter) to about 5 g/m$^2$, for example 0.8 g/m$^2$ to about 4 g/m$^2$. These ranges are obtainable from the formulations described herein. For example, a thin layer of about 1 to about 4 microns thick with a coverage of about 2.5 to about 2.8 g/m$^2$ would contain from about 30% to about 35% to about 40% or 45% by weight, based on the total weight of the layer, of the light absorbing composition.

More than one light absorbing layer may be used in the present invention wherein the light absorbing layers either have the same composition or wherein two or more light absorbing layers have different compositions. For example, different layers may contain the same or different polymeric binder, the same or different UVA, the same or different concentration of UVA, and the different layers may be the same of different thickness.

Different light absorbing layers may also contain a different co-additive, for example a dye, pigment or other stabilizer or processing aid, or a different concentration of co-additive.

When more than one light absorbing layer is present, it is generally desirable that thinner films be used, for example, from about 0.1 to about 50 microns thick.

UVAs useful in the invention are selected from hydroxyphenylbenzotriazole, benzophenone, benzoxazone, α-cyanoacrylate, oxanilide, tris-aryl-s-triazine, formamidine, cinnamate, malonate, benzilidene, salicylate and benzoate UVAs.

For Example, the UVA comprises a hydroxyphenylbenzotriazole, benzophenone, α-cyanoacrylate, oxanilide, tris-aryl-s-triazine or formamidine UVA. For example, the UVA comprises a compound selected from hydroxyphenylbenzotriazole, benzophenone and tris-aryl-s-triazine UVAs.

More than one UVA may be present. The UVA, and any other component in the formulation, is incorporated along with the binder into the light absorbing layer formulation using well known methods which are commonly practiced in the formulation of polymer and coating compositions. Such methods include blending, extrusion, compression molding, Brabender melt processing, injection molding, impregnation, suspension, dispersion or dissolution, typically used methods include blending, extrusion, Brabender melt processing, suspension, dispersion or dissolution.

As some photochromic colorants are sensitive to, and can be charged by, certain wavelengths of visible light, for example, higher energy visible light near 400 to 500 nm, dyes and pigments may be used as part of the light absorbing composition. When such components are used, the total concentration of the light absorbing composition, that is the combined weight of the UVAs and dyes or pigments, remains from about 1 to about 60% by weight, for example greater than 30% by weight, for example about 35-60% by weight, based on the total weight of the layer. It is also essential that the color change of the photochromic colorant remain visible.

For example, one embodiment of the invention, the light absorbing composition also contains, in addition to the UVA, an additional component selected from dyes, organic pigments, inorganic color pigments, metallic effect pigments, metal oxide effect pigments and non-metal oxide effect pigments, incorporated using well known methods, wherein the total amount of all the components in the light absorbing composition are present from about 1 to about 60% by weight, based on the total weight of the layer.

The binder of the light absorbing layer typically comprises commercially available wax or naturally occurring or synthetic polymer.

For example, the binder of the light absorbing layer may comprise a wax, gelatin, natural rubber, cellulose or chemically modified derivatives thereof, such as cellulose acetates, propionates and butyrates, the cellulose ethers such as methyl cellulose and also colophonium resins and derivatives.

The binder may also comprise a thermoplastic, elastomeric, thermoset, elastomeric, inherently crosslinked or crosslinked polymer. Examples of such thermoplastic, elastomeric, thermoset, elastomeric, inherently crosslinked or crosslinked polymers include, but are not limited to, polyolefin, polyamide, polyurethane, polyacrylate, polyacrylamide, polycarbonate, polystyrene, polyvinyl acetates, polyvinyl alcohols, polyester, halogenated vinyl polymers such as PVC, alkyd resins, epoxy resins, unsaturated polyesters, unsaturated polyamides, polyimides, fluorinated polymers, silicon containing, carbamate polymers and blends and copolymers thereof.

Typically, the binder is a binder which is commonly used in the art of thermal transfer printing or ink jet printing.

The light absorbing layer may also comprise common additives such as antioxidants, hindered amines, phosphites or phosphonites, benzofuran-2-ones, thiosynergists, polyamide stabilizers, metal stearates, nucleating agents, fillers, lubricants, emulsifiers, dyes, pigments, dispersents, optical brighteners, flame retardants, antistatic agents, and the like or mixtures thereof.

One embodiment of the invention relates to the process of applying the light absorbing layer to a substrate comprising the photo-chromic colorant via a thermal transfer printing or ink jet printing process. Thermal transfer printing herein refers to both the direct application from inked film to target substrate via a standard thermal transfer print head as well as the indirect transfer onto an intermediate substrate followed by a hot stamp or hot roller application of the image.

The light absorbing layer is conveniently applied by common printing methods such as thermal transfer or ink jet processes. Low melting carriers, for example, blends of waxes and ethylene vinyl acetate are convenient binders for thermal transfer processes. For example, a composition comprising the binder and UVA of the invention is coated onto a carrier ribbon, such as a PET carrier ribbon, and printed onto a substrate comprising the photo-chromic colorant. When applied via an ink jet process, the binder and UVA are part of a liquid composition which will generally comprise solvents, such as water and/or organic solvents, as typically encountered with ink jet inks and other ink jet formulations.

In either thermal transfer or ink jet applications, the composition from which the light absorbing layer is formed may optionally contain any other additives or adjuvants common in the respective technology. Examples of commonly occurring materials found in ink jet applications can be found, for example, in US Pat. Appl. Pub. No. 2005/0032931, which is incorporated herein in its entirety by reference.

Another embodiment of the invention relates to the composition that coats a thermal transfer ribbon which comprises the binder and UVA of the light absorbing layer, or the liquid composition useful in an inkjet process comprising the binder and UVA of the light absorbing layer.

Another embodiment relates to the thermal transfer ribbon coated with the composition which comprises the binder and UVA of the light absorbing layer.

A particular embodiment provides a temperature time indicator (TTI) which comprises a composition of the present invention containing a light absorbing layer adhered to an underlying substrate containing a photo-chromic colorant conditions, and have predictable and appropriate rates of both UV activation and color reversion.

U.S. Pat. No. 7,081,364, already incorporated by reference, discloses examples of colorants of value as the photo-chromic colorant of this invention. Many other photo-chromic dyes and pigments are of course known and may also be used for the purposes described herein. Compositions comprising these colorants can be applied via a printing process.

A particular example of a class of pigments useful as the photo-chromic colorant is the spiropyranes, one example of which is shown below:

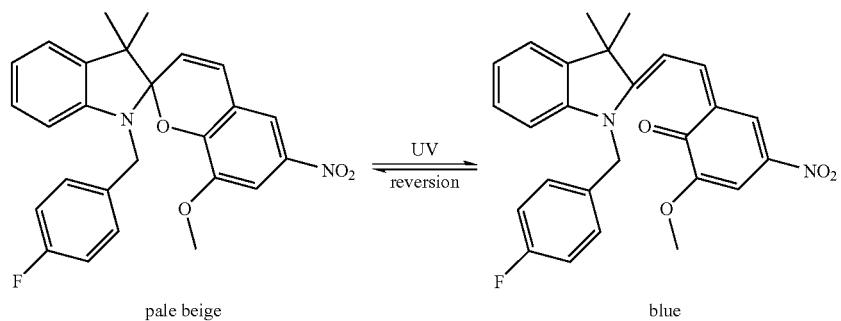

pale beige          blue which photo-chromic colorant has been activated by exposure to UV light to undergo a reversible color change, wherein the rate of color reversion is dependent on temperature, wherein the ultraviolet light and/or visible light absorbing layer comprises a binder as described above and from about 1 to about 60% by weight, for example about 35-60% by weight, based on the total weight of the layer of an ultraviolet light absorber selected from hydroxyphenylbenzotriazole, benzophenone, benzoxazone, α-cyanoacrylate, oxanilide, tris-aryl-s-triazine, formamidine, cinnamate, malonate, benzilidene, salicylate and benzoate UVAs.

Also provided is the process of preparing a TTI which process comprises irradiating a substrate containing a photo-chromic colorant and then immediately applying via thermal transfer or ink jet a light absorbing layer as described herein.

An advantage of the present light absorbing layer and processes herein is that the steps of (i) UV activating and (ii) thermal transfer and/or inkjet printing can be carried out in a fast and flexible manner which allows for quick and convenient methods to make the entire TTI ready for use which method can be directly integrated into the packaging line providing efficiencies and cost savings through, for example increased packaging line speeds and greater control over TTI activation.

The TTI may conveniently be a label or part of a label which is adhered to a package containing a perishable item.

The TTI may also be directly formed on the surface of an article or packaging material by, for example, applying onto, such as by coating or printing, or incorporating into the article or packaging material a photo-chromic colorant, exposing the colorant to UV light to effect the desired color change and then immediately, meaning as soon as practically possible, applying the light absorbing layer thereon via a thermal transfer of ink jet process.

The photo-chromic colorant is a photo-chromic dye or pigment. A variety of photo-chromic dyes and pigments are known and many are commercially available. The photo-chromic colorant chosen must be stable to the processing The present invention provides for UV-VIS filter compositions (the light absorbing layer) and high speed in line printing of UV-VIS filters, to protect light-sensitive materials such as time-temperature indicators or photo chromic inks. These filter compositions can be coatings or inks for thermal transfer, hot stamp, inkjet printing or other high speed in line methods of transferring the filter over the light-sensitive material. In the case of a filter for a photo chromic time temperature indicator (TTI), the TTI is typically charged and the filter (the light absorbing layer) is immediately printed over the TTI to protect it from light.

The present light absorbing layer offers many advantages over the heat transferable protective overcoat of U.S. Pat. No. 6,855,666. Whereas U.S. Pat. No. 6,855,666 provides a protective overcoat containing 2-20% of certain UV absorbing triazine compounds, the present invention provides a layer which may contain a higher level of UV absorber (up to 60 weight %) allowing for thinner film layers, uses of a variety of UV absorbers, e.g., benzotriazoles, benzophenones etc., is not limited to heat transferable protective overcoat, can also be ink jet printed, provides for high speed in line transfer of the protective filter and, is applied to substrates for protection of light-sensitive materials such as TTI and photo chromic inks, in particular, substrates comprising photo-chromic pigments.

To date, the art lacks an effective UV-VIS filter for the protection of a TTI based on photo chromic activity.

The invention allows higher amounts of UV absorber that can be incorporated into the filter composition than demonstrated in prior art. This means that the UV-VIS filter can provide excellent protection even when it is very thin, making filters printed by thermal transfer, inkjet and other printing methods much more practical.

The present invention facilitates the easy manufacture of reliable and simple photo-chromic Time and Temperature Indicators which can be readily manufactured and activated directly on a substrate in connection with printing of the substrate, and suitably at the time of packaging of the final product which is to be monitored. The substrate can be a label or packaging material, which may comprise plastics or other polymers, paper, cardboard, metal or glass.

EXAMPLES

Example 1

Light absorbing layers in the form of thermal transfer composition is prepared.

| Composition | Grams Wet | Grams Dry | % Dry |
|---|---|---|---|
| S-NAUBA 5021, Carnauba wax | 5 | 5 | 40 |
| CGL 777 MPA (70% in PM Acetate) | 7.1 | 5 | 40 |
| Toluene | 27.9 | 0 | 0 |
| ELVAX 210 (30% in Toluene) | 8 | 2.4 | 20 |

This composition above is mixed and coated onto a PET carrier ribbon using standard coating formulation and application techniques, then printed by thermal transfer, onto labels containing an ink that is sensitive to UV-VIS radiation. The composition is used in either a single-layer construction or multi-layer construction on the PET carrier ribbon.

Example 2

The label of example 1 is coated first with an adhesion promoting layer and then the composition of Example 1 is applied printed thereon.

Example 3

The following composition is prepared via standard coatings formulation techniques and applied to a PET carrier ribbon and printed as above in Example 1 or 2.

| | Wet% | Dry% |
|---|---|---|
| TINUVIN 477DW (tris-resorcinol triazine UVA) | 50% | 14.3% UVA, |
| (20% active UV absorber encapsulated | (10% UV absorber, | 14.3% polymer |
| 1:1 in a polymer and dispersed in water) | 10% polymer, 30% water) | |
| GLASCOL 44 (acrylic resin) | 10% | 14.3% |
| MICHEMLUBE 260 (packaging film material containing synthetic polymers and waxes) | 40% | 57% |

What is claimed:

1. A time temperature indicator (TTI) comprising a light absorbing layer which is adhered to an underlying substrate, which underlying substrate comprises a photo-chromic colorant,
   which photo-chromic colorant has been activated by exposure to UV light to undergo a reversible color change, which color reversion occurs at a rate that is dependent on temperature and/or time,
   wherein the light absorbing layer is applied to the underlying substrate immediately after the photo-chromic colorant has been activated by exposure to UV light,
   wherein the light absorbing layer comprises a binder, said binder comprising a wax, a natural polymer and/or a synthetic polymer and
   from about 35 to about 60% by weight, based on the total weight of the layer, of a light absorbing composition
   which light absorbing composition comprises one or more components selected from the group consisting of hydroxyphenylbenzotriazole, benzophenone, benzoxazone, α-cyanoacrylate, oxanilide, tris-aryl-s-triazine, formamidine, cinnamate, malonate, benzilidene, salicylate and benzoate ultraviolet light absorbers
   and wherein the light absorbing layer is sufficiently transparent in the visible light region to allow the reversible color change of the photochromic material to be visible.

2. The TTI according to claim 1, wherein the light absorbing layer also contains an additional component selected from dyes, organic pigments, inorganic color pigments, metallic effect pigments, metal oxide effect pigments and non-metal oxide effect pigments, wherein the total amount of all the components in the light absorbing composition are present from about 35 to about 60% by weight, based on the total weight of the layer.

3. The TTI according to claim 1, wherein the light absorbing layer is from about 0.1 to about 1,000 microns thick.

4. The TTI according to claim 1, wherein the light absorbing layer is from about 2 to about 100 microns thick.

5. The TTI according to claim 1, wherein the light absorbing layer is from about 0.1 to about 50 microns thick.

6. The TTI according to claim 1, wherein the light absorbing layer comprises a compound selected from hydroxyphenylbenzotriazole, benzophenone, α-cyanoacrylate, oxanilide, tris-aryl-s-triazine and formamidine ultraviolet light absorbers.

7. The TTI according to claim 1, wherein the light absorbing layer comprises a compound selected from hydroxyphenylbenzotriazole, benzophenone and tris-aryl-s-triazine ultraviolet light absorbers.

8. The TTI according to claim 1, wherein the binder of the light absorbing layer comprises a wax, gelatin, natural rubber, cellulose, cellulose acetate, propionate and butyrate, cellulose ether, or a synthetic thermoplastic, elastomeric, thermoset, inherently crosslinked or crosslinked polymer.

9. The TTI according to claim 8, wherein the synthetic thermoplastic, elastomeric, thermoset, inherently crosslinked and crosslinked polymers are selected from polymers of the group, polyolefin, polyamide, polyurethane, polyacrylate, polyacrylamide, polycarbonate, polystyrene, polyvinyl acetates, polyvinyl alcohols, polyester, halogenated vinyl polymers such as PVC, alkyd resins, epoxy resins, unsaturated polyesters, unsaturated polyamides, polyimides, fluorinated polymers, silicon containing polymer, carbamate polymers and copolymers thereof.

10. The TTI according to claim 1 comprising more than one light absorbing layer wherein the light absorbing layers have the same composition or wherein two or more light absorbing layers have different compositions.

11. A temperature time indicator according to claim 1 which is comprised by a label or a packaging material.

* * * * *